US006726714B2

(12) United States Patent
DiCaprio et al.

(10) Patent No.: US 6,726,714 B2
(45) Date of Patent: Apr. 27, 2004

(54) STENT DELIVERY SYSTEM

(75) Inventors: Fernando DiCaprio, St. Paul, MN (US); Jan D. Seppala, Maple Grove, MN (US); Kyle P. Taylor, Brooklyn Park, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 236 days.

(21) Appl. No.: 09/925,385

(22) Filed: Aug. 9, 2001

(65) Prior Publication Data

US 2003/0033000 A1 Feb. 13, 2003

(51) Int. Cl.$^7$ .................................................. A61F 2/06
(52) U.S. Cl. ...................................................... 623/1.11
(58) Field of Search ............................... 623/1.11, 1.23; 604/148, 508, 509, 510; 606/108, 191, 194, 192, 198, 195

(56) References Cited

U.S. PATENT DOCUMENTS

| 2,690,595 A | 10/1954 | Raiche |
| 4,271,839 A | 6/1981 | Fogarty et al. |
| 4,327,736 A | 5/1982 | Inoue |
| 4,328,056 A | 5/1982 | Snooks |

(List continued on next page.)

FOREIGN PATENT DOCUMENTS

| EP | 0 257 091 | 3/1988 |
| EP | 0 274 411 | 7/1988 |
| EP | 0 274 846 | 7/1988 |
| EP | 0 420 488 A1 | 4/1991 |

(List continued on next page.)

OTHER PUBLICATIONS

US 4,748,981, 6/1988, Crittenden (withdrawn)

Julio C. Palmaz et al., *Expandable Intraluminal Graft: A Preliminary Study, Work in Progress*, From Departments of Radiology and Pathology, University of Texas Health Science Center at San Antonio and Memorial Medical Center, Corpus Christi, Texas, RADIOLOGY vol. 356, No. 1, pp. 73–77.

Kim et al., *Mechanical and Transport Properties of Coextruded Films*, Journal of Applied Science, vol. 29, 1984, pp. 2359–2382.

May et al., *Polyvinyl and Vinyl Copolymers*, Modern Plastics Encyclopedia, 1986–1987, pp. 82.

Daniel O. Adams, *BME, PTCA Balloon Materials, Their Characteristics and Impac on Catheter Selection*, Sales Training Technical Notes.

*Tailoring Expansion Properties of Balloons for Medical Devices*, Health Watch, Prepared Oct. 25, 2994 at 3:04, pp. 3.

Avanindra Jain et al., *Effect of Inflation Pressures on Coronary Angioplasty Balloons*, The American Journal of Cardiology, Jan. 1, 1986, vol. 57, pp. 26–28.

U.S. patent application Ser. No. 09/668,496, Yang, filed Sep. 22, 2000.

U.S. patent application Ser. No. 09/383,174, Lorentzen Cornelius et al., filed Aug. 25, 1999.

U.S. patent application Ser. No. 08/917,027, Lorentzen Cornelius et al., filed Aug. 22, 1997.

Dialog Patent Search, Nov. 3, 1994.

Julio C. Palmaz et al., 156 *Radiology* 73 (1985), *Expandable Intraluminal Graft: A Preliminary Study*.

*Primary Examiner*—Michael J. Milano
(74) *Attorney, Agent, or Firm*—Vidas, Arrett&Steinkrays PA (57) ABSTRACT

This invention relates to catheters used for delivering medical devices. The catheter incorporates sleeves which aid in containing the medical device on the catheter, wherein the sleeves have portions comprising high modulus material to aid in the function of the sleeves.

23 Claims, 6 Drawing Sheets

U.S. PATENT DOCUMENTS

| | | |
|---|---|---|
| 4,338,942 A | 7/1982 | Fogarty |
| 4,403,612 A | 9/1983 | Fogarty |
| 4,423,725 A | 1/1984 | Baran et al. |
| 4,576,871 A | 3/1986 | Oestreich |
| 4,608,984 A | 9/1986 | Fogarty |
| 4,637,396 A | 1/1987 | Cook |
| 4,649,914 A | 3/1987 | Kowalewski |
| 4,702,252 A | 10/1987 | Brooks et al. |
| 4,733,665 A | 3/1988 | Palmaz .................... 128/343 |
| 4,735,665 A | 4/1988 | Miyauchi et al. |
| 4,740,207 A | 4/1988 | Kreamer ..................... 623/1 |
| 4,744,366 A | 5/1988 | Jang |
| 4,763,654 A | 8/1988 | Jang |
| 4,787,388 A | 11/1988 | Hofmann |
| 4,848,343 A | 7/1989 | Wallsten et al. |
| 4,875,480 A | 10/1989 | Imbert |
| 4,885,194 A | 12/1989 | Tight, Jr. et al. |
| 4,932,958 A | 6/1990 | Reddy et al. |
| 4,950,227 A * | 8/1990 | Savin et al. ................ 606/192 |
| 4,983,167 A | 1/1991 | Sahota |
| 4,990,139 A | 2/1991 | Jang |
| 4,994,033 A | 2/1991 | Shockey et al. |
| 5,007,926 A | 4/1991 | Derbyshire ..................... 623/1 |
| 5,026,377 A | 6/1991 | Burton et al. |
| 5,037,392 A | 8/1991 | Hillstead |
| 5,049,131 A | 9/1991 | Deuss |
| 5,049,132 A | 9/1991 | Shaffer et al. |
| 5,057,092 A | 10/1991 | Webster, Jr. |
| 5,071,406 A | 12/1991 | Jang |
| 5,090,958 A | 2/1992 | Sahota |
| 5,096,848 A | 3/1992 | Kawamura |
| 5,108,370 A | 4/1992 | Walinsky |
| 5,108,416 A * | 4/1992 | Ryan et al. ................ 606/194 |
| 5,116,318 A | 5/1992 | Hillstead |
| 5,158,548 A | 10/1992 | Lau et al. |
| 5,192,295 A | 3/1993 | Danforth et al. |
| 5,195,969 A | 3/1993 | Wang et al. |
| 5,226,880 A | 7/1993 | Martin |
| 5,226,889 A | 7/1993 | Sheiban |
| 5,242,399 A | 9/1993 | Lau et al. |
| 5,264,260 A | 11/1993 | Saab |
| 5,270,086 A | 12/1993 | Hamlin |
| 5,290,306 A | 3/1994 | Trotta et al. |
| 5,295,962 A | 3/1994 | Crocker et al. |
| 5,298,300 A | 3/1994 | Hosoi et al. |
| 5,304,132 A | 4/1994 | Jang |
| 5,304,198 A | 4/1994 | Samson |
| 5,306,250 A | 4/1994 | March et al. |
| 5,342,305 A | 8/1994 | Shonk |
| 5,344,401 A | 9/1994 | Radisch et al. |
| 5,344,402 A | 9/1994 | Crocker |
| 5,344,426 A | 9/1994 | Lau et al. |
| 5,358,487 A | 10/1994 | Miller |
| 5,378,237 A | 1/1995 | Boussignac et al. |
| 5,403,341 A | 4/1995 | Solar ..................... 606/198 |
| 5,405,380 A | 4/1995 | Gianotti et al. |
| 5,409,495 A | 4/1995 | Osborn |
| 5,415,635 A | 5/1995 | Bagaoisan et al. |
| 5,415,664 A | 5/1995 | Pinchuk |
| 5,441,515 A | 8/1995 | Khosravi et al. |
| 5,445,646 A * | 8/1995 | Euteneuer et al. .......... 606/193 |
| 5,447,497 A | 9/1995 | Sogard et al. |
| 5,453,090 A | 9/1995 | Martinez et al. |
| 5,458,615 A | 10/1995 | Klemm et al. |
| 5,470,313 A | 11/1995 | Crocker et al. |
| 5,478,320 A | 12/1995 | Trotta |
| 5,490,839 A | 2/1996 | Wang et al. |
| 5,507,768 A | 4/1996 | Lau et al. |
| 5,512,051 A | 4/1996 | Wang et al. |
| 5,534,007 A | 7/1996 | St. Germain et al. |
| 5,536,252 A | 7/1996 | Imran et al. |
| 5,545,209 A | 8/1996 | Roberts et al. |
| 5,587,125 A | 12/1996 | Roychowdhury |
| 5,591,222 A * | 1/1997 | Susawa et al. ................ 623/1 |
| 5,591,228 A | 1/1997 | Edoga |
| 5,632,760 A | 5/1997 | Sheiban et al. |
| 5,643,278 A * | 7/1997 | Wijay ....................... 606/198 |
| 5,653,691 A | 8/1997 | Rupp et al. |
| 5,676,654 A * | 10/1997 | Ellis et al. ................. 604/103 |
| 5,709,703 A | 1/1998 | Lukic et al. ................ 606/198 |
| 5,776,141 A * | 7/1998 | Klein et al. ............... 623/1.11 |
| 5,788,707 A | 8/1998 | Del Toro et al. .......... 606/108 |
| 5,800,517 A * | 9/1998 | Anderson et al. .......... 623/1.11 |
| 5,876,344 A * | 3/1999 | Baker et al. ................ 600/463 |
| 5,921,958 A * | 7/1999 | Ressemann et al. ..... 604/96.01 |
| 5,961,536 A * | 10/1999 | Mickley et al. ............ 606/194 |
| 6,068,634 A * | 5/2000 | Lorentzen Cornelius et al. ........................ 623/1.11 |
| 6,120,533 A * | 9/2000 | Fischell ..................... 623/1.11 |
| 6,238,406 B1 * | 5/2001 | Ellis et al. ................. 606/167 |
| 6,270,504 B1 * | 8/2001 | Lorentzen Cornelius et al. ........................ 606/108 |
| 6,461,326 B1 * | 10/2002 | Yang et al. ............... 604/96.01 |
| 6,517,547 B1 * | 2/2003 | Feeser et al. ............... 606/108 |
| 6,565,595 B1 * | 5/2003 | DiCaprio et al. .......... 623/1.11 |
| 2003/0060832 A1 * | 3/2003 | Guinan et al. .............. 606/108 |

FOREIGN PATENT DOCUMENTS

| | | |
|---|---|---|
| EP | 0 442 657 A2 | 8/1991 |
| EP | 0 442 657 | 8/1991 |
| EP | 0457 456 | 11/1991 |
| EP | 0 540 858 | 5/1993 |
| EP | 0 420 488 B1 | 7/1993 |
| EP | 0 553 960 A1 | 8/1993 |
| EP | 0 553 960 | 8/1993 |
| EP | 0 582 870 | 2/1994 |
| EP | 0 627 201 | 12/1994 |
| EP | 0 699 451 | 3/1996 |
| EP | 707 837 A1 | 4/1996 |
| EP | 0 707 837 | 4/1996 |
| EP | 0990427 A2 | 9/1999 |
| WO | WO 90/05554 | 5/1990 |
| WO | WO 92/08512 | 5/1992 |
| WO | WO 92/19440 | 11/1992 |
| WO | WO 93/19703 | 10/1993 |
| WO | WO 95/09667 | 4/1995 |
| WO | WO 95/22367 | 8/1995 |
| WO | WO 96/03072 | 2/1996 |
| WO | WO96/03072 A1 | 2/1996 |
| WO | WO96/03092 A1 | 2/1996 |
| WO | WO 96/03092 | 2/1996 |
| WO | WO 96/04951 | 2/1996 |

* cited by examiner

STENT DELIVERY SYSTEM

FIELD OF THE INVENTION

This invention relates to catheters used for delivering medical devices. The catheter incorporates sleeves which aid in containing the medical device on the catheter, wherein the sleeves have portions comprising high modulus material to aid in the function of the sleeves.

BACKGROUND OF THE INVENTION

In typical PTCA procedures, a guiding catheter is percutaneously introduced into the cardiovascular system of a patient through a vessel and advanced through therein until the distal end thereof is at a desired location in the vasculature. A guidewire and a dilatation catheter having a balloon on the distal end thereof are introduced through the guiding catheter with the guidewire sliding through the dilatation catheter. The guidewire is first advanced out of the guiding catheter into the patient's coronary vasculature and the dilatation catheter is advanced over the previously advanced guidewire until the dilatation balloon is properly positioned across the lesion. Once in position across the lesion, the flexible, expandable, preformed balloon is inflated to a predetermined size with a liquid or gas at relatively high pressures, such as greater than about four atmospheres, to radially compress the arthrosclerotic plaque of the lesion against the inside of the artery wall and thereby dilate the lumen of the artery. The balloon is then deflated to a small profile so that the dilatation catheter may be withdrawn from the patients vasculature and blood flow resumed through the dilated artery.

In angioplasty procedures of the kind described above, there may be injury to or restenosis of the artery, which either necessitates another angioplasty procedure, a surgical by-pass operation, or some method of repairing or strengthening the area. To strengthen the area and help prevent restenosis, a physician can implant an intravascular prosthesis for maintaining vascular patency, commonly called a stent, inside the artery at the lesion. The stent is expanded to a larger diameter for placement in the vasculature, often by the balloon portion of the catheter.

Stents delivered to a restricted coronary artery, expanded to a larger diameter by a balloon catheter, and left in place in the artery at the site of a dilated lesion are shown in U.S. Pat. No. 4,740,207 to Kreamer, PCT Application No. 960 3092 A1, published Feb. 8, 1996, and U.S. Pat. No. 5,007,926 to Derbyshire, the content of which is incorporated herein by reference. Palmaz et al., 156 *Radiology* 73 (1985) and U.S. Pat. No. 4,733,665 describe introduction of a stent over a balloon catheter.

The present invention is particularly directed to improved arrangements and configurations of sleeves for releasably covering the ends of the stent to prevent the stent ends from flaring and snagging to better facilitate delivery thereof. Examples of stent retaining sleeves can be found in Savin U.S. Pat. No. 4,950,227, U.S. application Ser. No. 09/407, 836, filed Sep. 28, 1999 and U.S. application Ser. No. 09/668,496, filed Sep. 22, 2000

All US patents and applications all other published documents mentioned anywhere in this application are incorporated herein by reference in their entirety.

Without limiting the scope of the invention in any way, the invention is briefly summarized in some of its aspects below.

SUMMARY OF THE INVENTION

This invention concerns apparatus suitable for delivery of stents to body cavities. In general, stents are prosthetic devices which can be positioned within a body cavity, for example, a blood vessel of the body of a living human or in some other difficultly accessible place. The stent prosthesis is formed of a generally tubular body, the diameter of which can be decreased or increased. Stents are particularly useful for permanently widening a vessel which is either in a narrowed state, or internally supporting a damaged vessel. Such stents are typically introduced into the body cavity by use of a catheter. The catheter is usually of the balloon catheter type in which the balloon is utilized to expand the stent, which is positioned over the balloon, to place it in a selected location in the body cavity. The present invention is particularly directed to improved arrangements for releasably covering/securing the stent, particularly the ends thereof, to the catheter to prevent snagging of the stent ends and to facilitate delivery thereof. Depending on the type of stent used, the stent is held in place on the catheter and kept from flaring upward at its end(s) by means of at least one removable end covering means, or sock, over the stent, the stent having been fitted to the catheter over the balloon, as by crimping. Most specifically, this invention is directed to improved modifications of stent retaining sleeves.

In particular, the invention is directed to an improved stent delivery system designed to hold a stent over the balloon on a catheter, via the sleeve arrangements and to protect the stent from deformation, damage or premature release during delivery intraluminally, as well as snagging during transportation. It is also a purpose of the present invention to provide for easier and smoother removal of the sleeve retaining means. The stent is formed to its lowest geometrical diameter when loaded. The sleeves of the present invention incorporate high modulus compositions in the form of bands, which are positioned over the cone portion of the balloon on top of or beneath the socks and preferably bonded thereto. The sleeves aid in retaining the stent and holds the stent to the balloon (unexpanded) with little or no relative movement between the ID of the stent and the OD of the balloon/catheter arrangement. The bands are each preferably attached (adhered or welded) to the elastomeric socks or sleeves. One end of the sleeves cover the ends of the stent and the other end of the sleeves are respectively attached to the catheter. When the balloon under the stent is inflated, the bands, which are positioned on the tapered cone portion of the balloon, are driven primarily axially, resulting in the sleeves being pushed/pulled down the balloon cones to allow the stent to deploy. The positioning of the bands on the cones of the balloon allows for more of an axial force and movement of the socks when the balloon inflates rather then a radial force and provides a flatter profile as apposed to other arrangements. This allows for a steadier, smoother, more controlled removal of the sleeves instead of an abrupt release, which may happen with a primarily radial force. Since most stents which are deformed to a low diameter will increase in diameter somewhat after being deformed (spring back), the sleeves also somewhat prevent spring back and increase the friction fit between the stent and balloon.

The present invention contemplates a stent delivery system having stent retaining sleeves having a high modulus ring or band, preferably a polymeric or metal band, located along the body of the sleeve. The high modulus band gives the sleeve improved retraction properties while allowing the stent edges to deploy. The present invention allows the stent ends to deploy at lower pressures, while assuring full retractions of the sleeves.

Modifications to this embodiment are further described below.

DESCRIPTION OF THE PREFERRED EMBODIMENTS

While this invention may be embodied in many different forms, there are shown in the drawings and described in detail herein specific embodiments of the invention. The present disclosure is an exemplification of the principles of the invention and is not intended to limit the invention to the particular embodiments illustrated.

For the purposes of this disclosure, the term stent refers to stents, stent-grafts, grafts and other endoluminal prostheses whether self-expanding, balloon expandable, self-expanding and balloon expandable or otherwise expandable as are known in the art.

In addition to the over-the-wire embodiments (example also found in U.S. Pat. No. 5,980,533) shown in FIGS. 1–4, the inventive catheter system may also be provided in a rapid-exchange configuration. Examples of rapid-exchange catheters may be found in U.S. Pat. Nos. 5,534,007 and 5,833,706. The inventive stent delivery systems may also be made in fixed wire form. Examples of fixed-wire catheters may be found in U.S. Pat. No. 5,702,364.

The system may be adapted for use with a medical device such as a stent, for example, a self-expanding, balloon expandable or combination self-expanding and balloon expandable stent. The system may also be used for delivery of other medical devices for use in the body as well including, but not limited to, ultrasonic devices, laser devices, vena cava filters, implantable drug delivery devices and the like.

The inventive medical systems disclosed herein may also be provided with any of the features disclosed in U.S. Pat. No. 6,096,056, U.S. Pat. No. 6,068,634, U.S. Pat. No. 6,036,697, U.S. Pat. No. 6,007,543, U.S. Pat. No. 5,968,069, U.S. Pat. No. 5,957,930, U.S. Pat. No. 5,944,726, U.S. Pat. No. 5,653,691 and U.S. Pat. No. 5,534,007.

The stent delivery system may also comprise various coatings as are known in the art, including lubricious coatings to facilitate movement of the various parts of the system, as well as collagen-type coatings. More information concerning suitable coatings may be found in U.S. Pat. No. 5,443,907, and U.S. application Ser. Nos. 08/382,478, 09/306,939 and 09/316,502.

Figure 1:
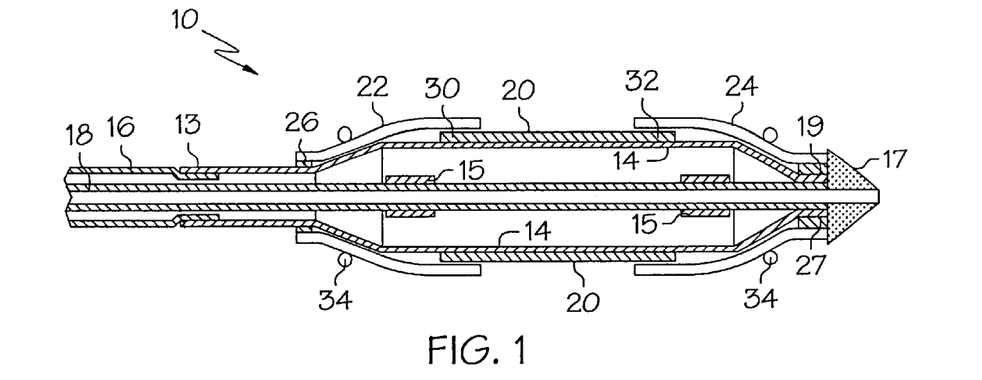
FIG. 1 is a cross-sectional view, in longitudinal section, of the distal end portion of a balloon catheter having a stent fixed to the catheter by being crimped thereto over the balloon, the ends of the stent being covered by a first embodiment of the invention.
Figure 2:
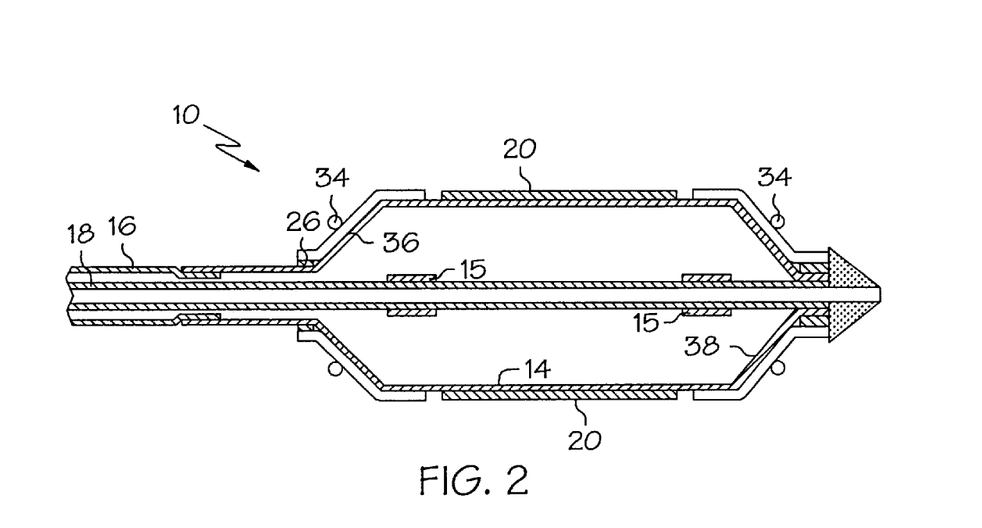
FIG. 2 is similar to FIG. 1 in which the balloon is expanded and the stent has been released.

Referring to FIGS. 1 and 2, a stent delivery system 10 includes a catheter such as an over-the-wire or rapid exchange. Balloon catheters are preferred herein as best examples of catheters having an expandable distal end portion constructed and arranged for expanding the outer diameter of the catheter from a contracted state to an expanded state. FIGS. 1 and 2 shows a catheter 10 having a outer shaft 16, a guide wire lumen 18 with marker band secured thereto 15 and a distal tip 17. A balloon 14 is fixed to the distal end of the catheter by adhesive or welding attachment of the proximal end 13 to the outer shaft 16 of the catheter and the distal end 19 to the inner shaft 18 of the catheter. Other arrangements known in the art may be used. Balloon 14 is shown in FIG. 1 in its contracted state and in FIG. 2 in its expanded state. A stent 20 is held about balloon 14 by two overlying retaining sleeves, or socks, 22 and 24, which cover the ends 30, 32 of the stent, respectively.

Various types of stents may be used with balloon expansion. For example, the stent may be a self-expanding stent which upon release self-expands and is further expanded or is merely aided in release by balloon expansion from the sleeves. Such stents may self-expand elastically or may be thermally induced such as stents formed of nitinol or other shape memory metals or materials.

Any kind of stent may be delivered by the system of the invention, including plastically deformable or elastically deformable, and they may be of any configuration or structure so long as they can be loaded at a low diameter and deployed at a larger diameter, i.e., have a contracted condition and being expandable to an expanded condition of large diameter.

Stent 20 may be any of the various types known in the art, either balloon expandable or self-expandable. Exemplary stents are shown in U.S. Pat. No. 4,735,665; U.S. Pat. No. 4,950,227; EPO application 707 837 A1, and U.S. Pat. No. 5,445,646. All of these patents are incorporated herein by reference and are intended to be exemplary only and not limiting. Various materials including stainless steel, tantalum, shape memory alloys and plastic may be used.

Stent 20 is radially compressed, as by crimping to a contracted condition, against balloon 14 to a relatively small loaded diameter having an OD of 0.044 inches for example, although it has a larger released diameter in the expanded condition. Various sized stents may be used Sleeves 22 and 24 may be formed of any material suitable for catheter sleeves. By way of example, sleeves may be made of an expandable material, including a broad class of elastomers, such as urethanes, styrenics, silicones, natural rubbers, nylons, segmented polyamide-polyether-polyesters sold under the Pebax® (Pebax), polyesters (Arnitel), latex, polyether amide, polyolefin copolymer (POC) or Surlyn™, by way of example only. The material should be formable into a thin walled tube. Only one sleeve may be provided at one end of the stent, such as the distal end. However, the use of a pair of sleeves, one at each end of the stent, is typical.

For example, polyurethane tubing or the like can be used, having a Shore D scale hardness of preferably 70A-55D and having, for example, an ID of 0.032–0.038 inches and a wall thickness of 0.002–0.004 inches. Of course, the ID and wall thickness may be dictated by the size of stent being used. Sleeves 22 and 24 are axially connected along catheter 10 to the proximal end of balloon 14 at 26 and to the distal end of balloon 14 at 27 by means of adhesive 26, 27 or welding. Other methods of connecting the sleeves to the catheter such as welding or by utilizing a frictional gripping force which is produced due to the elasticity of the sleeve, all methods are well known in the art.

Sleeves 22 and 24 overlap stent 20 at each of its ends 30 and 32, respectively. Rings or bands 34 are affixed around the sleeves 22, 24 via adhesion, such as an adhesive, or welding. The bands 34 may be embedded into the sleeve. The bands are made of a higher modulus material relative to the sleeve material. The band material may have higher strength and less elongation than the material of the sleeve. The bands also may be any material which forms a closed curve or any polygonal structure, or a combination of the two. In an alternative embodiment, the bands may also be discontinuous and forming generally circular or polygonal shapes. Preferably, the bands are made of a material which effectively retains a substantially annular shape. One function of the rings is to more effectively and smoothly draw the sleeve off of the ends of the stent, by creating more axial movement of the ring 34.

Bands 34 are positioned over the cone portion of the balloon 14, in this example mid-way up the cone, when the balloon is in its collapsed configuration. By way of example, bands 34 may have Shore D scale hardness of greater than 55, such as with PEBAX, PET, nylon, plastic, such as polyimide or polyethylene, or metal, such as platinum, gold, stainless steel or nitinol.

Referring to FIG. 2, in its expanded state balloon 14 has an enlarged diameter with tapered cone portions 36 and 38 at each end thereof. Stent 20 is released from sleeves 22 and 24 upon expansion of balloon 14 due to the axial/radial force created by balloon causing the sleeves to recede. The sleeves may recede away from the stent in any manner.

In at least one manner, the bands draw the sleeves gradually outward, bunching the sleeves between the bands 34 and the fixed position of the sleeves on the catheter. The combination of radial and axial forces are applied to the ring 34. Since the rings resist the radial force, they are driven primarily axially, dragging the sleeves off of the ends of the stent and balloon, while maintaining the sleeves close to the balloon. The increased axial pressure allows for a more controlled and steady release of the stent and balloon, as opposed to a sudden release which may happen when the primary force on the sleeve is in the radial direction. As seen in FIG. 2 the stent deploys. The sleeves contract about balloon 14 when it is deflated. Deflation allows balloon 14 and sleeves 22 and 24 along with catheter 10 to be axially removed from the body.

In assembling polyurethane sleeves, they can be temporarily swelled by exposure to a solvent such as toluene, alcohol, or others as known in the art, or lubricated then pushed on the ends of the stent. The sleeves are then bonded to the balloon ends with an adhesive or the like. The sleeves may also be lubricated to prevent resistance when in use.

Figure 3A:
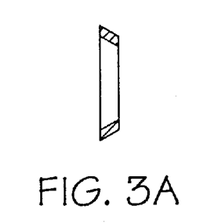
FIGS. 3a–c are side views of various ring configurations.
Figure 3B:
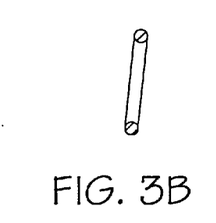
Figure 3C:
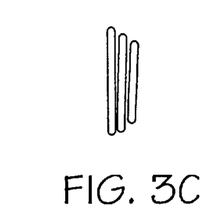

Other embodiments are within the claims to this invention. For example, referring to FIGS. 3A–C, the bands in the Figures may take the form of a shaped ring (FIG. 3A), shaped to surround the cone of the balloon, rings (FIG. 3B), or wire coils (FIG. 3C). The spiral of the coil may be cut only partially into the body as a spiral cut or it may be cut all the way through as shown. The cross-section of the bands can take any form, such as squares or any regular polygon as well.

Figure 4:
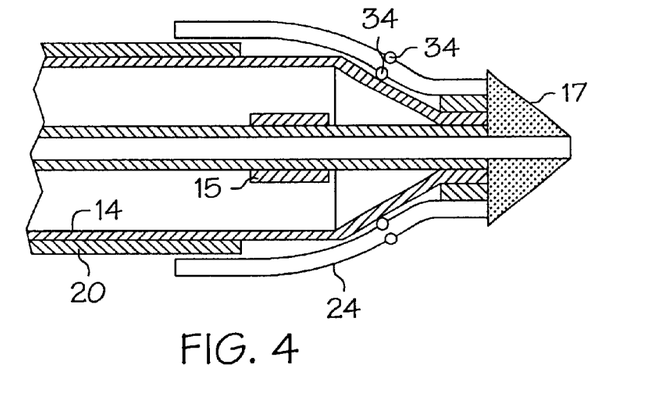
FIG. 4 is a view of a modification of the embodiment shown in FIG. 1.
Figure 5:
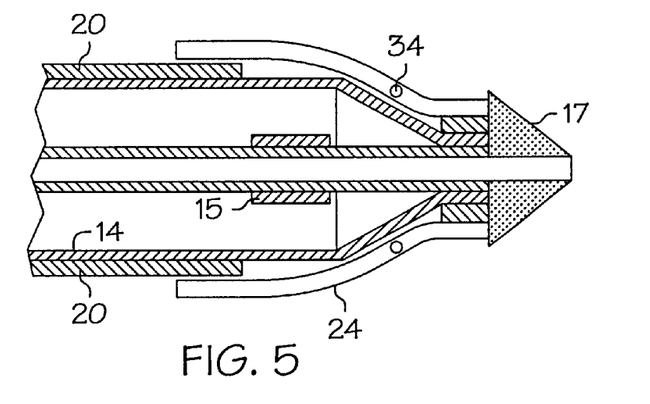
FIG. 5 is a view of a modification of the embodiment shown in FIG. 1.
Figure 6:
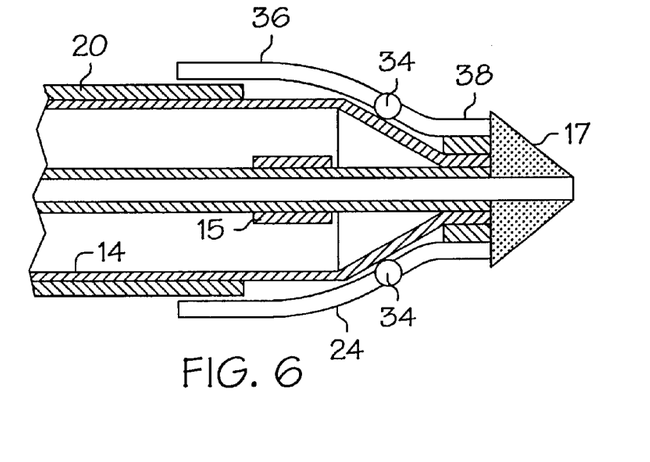
FIG. 6 is a view of a modification of the embodiment shown in FIG. 1.

FIGS. 4–6 show different positions and configurations for the bands. Only the distal end of the catheter is shown for illustrative purposes. It should be understood that two sleeves, one on either end of the balloon, may be utilized.

In FIG. 4, the sleeve 24 has two bands 34, one being partially embedded on the inside of the sleeve and one partially embedded on the outside of the sleeve 24. Preferably, the bands are in mirroring positions relative to the sleeve 24 over the cone portion.

In FIG. 5, the bands 34 are substantially embedded within the sleeve 24. This allows the profile of the catheter to be reduced.

In FIG. 6, the sleeves comprise two portions 36, 38 separated by the bands 34. In this embodiment, portions 36, 38 of the sleeve 24 are attached on either side of the band 34 via adhesion or welding or via an integral connection. It should be understood that the bands need not be spherical as shown. Various cross-sectional shapes may be incorporated FIGS. 7–12 illustrate further embodiments of the invention. These figures show two-piece sleeves, wherein one piece comprises material as described above in reference to band 34, that being high modulus material, and one piece comprises material as described above in reference to sleeves 22 and 24, that being lower modulus material. Hereafter, the two pieces which make up the sleeves will be referred to as high modulus (HM) bands and low modulus (LM) bands. The use of the words "low" and "high" are meant to indicate the level of modulus for the two pieces of the sleeves, each relative to the other. For example, the HM bands have a higher modulus relative to the LM bands.

Figure 7:
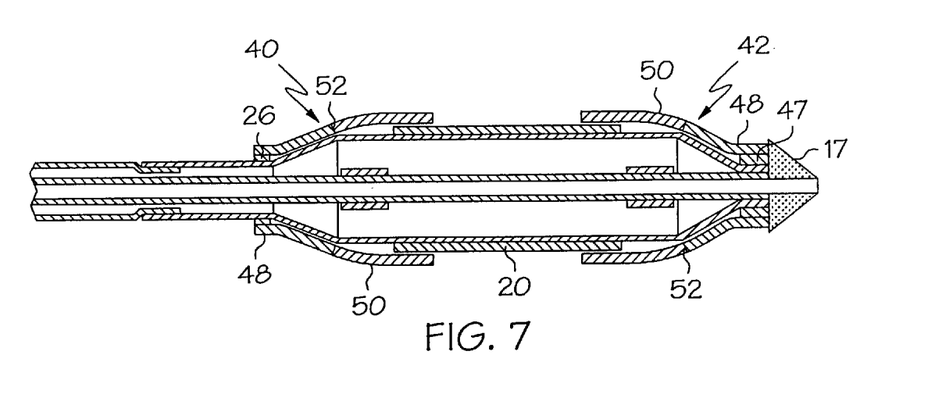
FIG. 7 is a cross-sectional view, in longitudinal section, of the distal end portion of a balloon catheter having a stent fixed to the catheter by being crimped thereto over the balloon, the ends of the stent being covered by a further embodiment of the invention.
Figure 8:
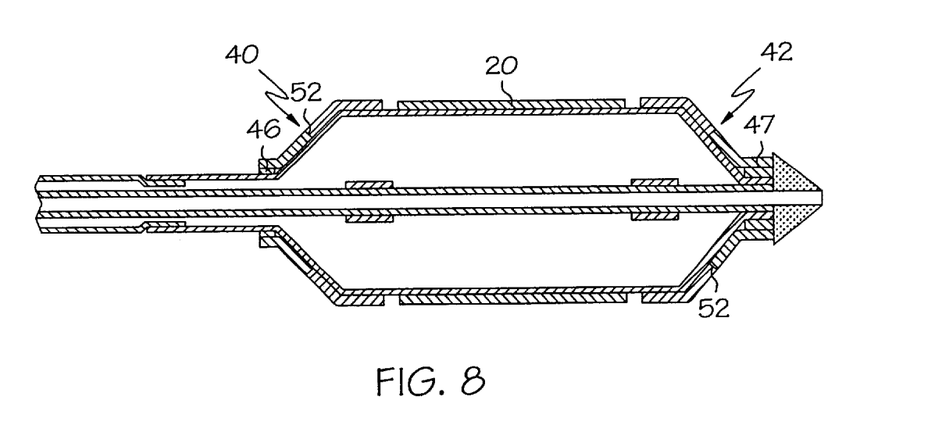
FIG. 8 is similar to FIG. 7 in which the balloon is expanded and the stent has been released.

In FIGS. 7–8, as in FIGS. 1–2, a balloon catheter is shown in its collapsed form and in its expanded form, respectively. The stent retaining sleeves 40, 42 comprise two pieces. Sleeves 40, 42 comprise a HM band 48 and a LM band 50. In this embodiment, one end of the HM bands 48 is connected to the balloon at 46 and 47 in the same manner as described above, while the remaining ends of the HM bands are in abutting connection 52 with the LM bands 50. The remaining ends of the LM bands 50 cover the corresponding end margins of the stent 20.

FIGS. 9–12 show different positions and configurations for the sleeves. Only the distal end of the catheter is shown for illustrative purposes. It should be understood that two sleeves, one on either end of the balloon, may be utilized.

Figure 9:
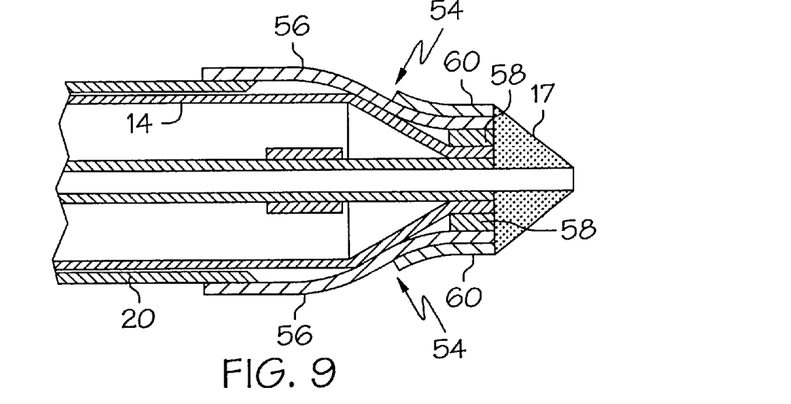
FIG. 9 is a view of a modification of the embodiment shown in FIG. 7.

In FIG. 9, sleeve 54 comprises two pieces. The LM band 56 extends from being attached via conventional means to the balloon at point 58 to a point over the margin of the stent 20. The HM band 60 is attached to the LM band 56 over point 58 extending partially up the cone portion of the balloon.

Figure 10:
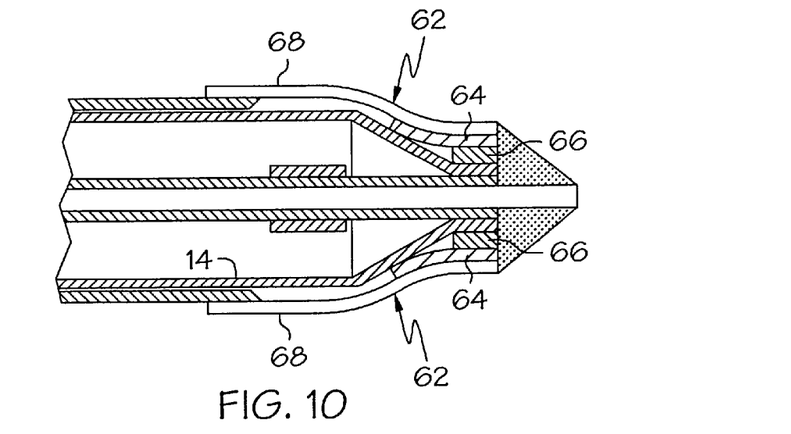
FIG. 10 is a view of a modification of the embodiment shown in FIG. 7.

In FIG. 10, sleeve 62 comprises two pieces. The HM band 64 extends from being attached via conventional means to the balloon at point 66 to a point partially up the cone portion of the balloon 14. The LM band 68 is attached to the HM band 64 over point 66 extending along the balloon 14 over the margin of the stent 20.

Figure 11:
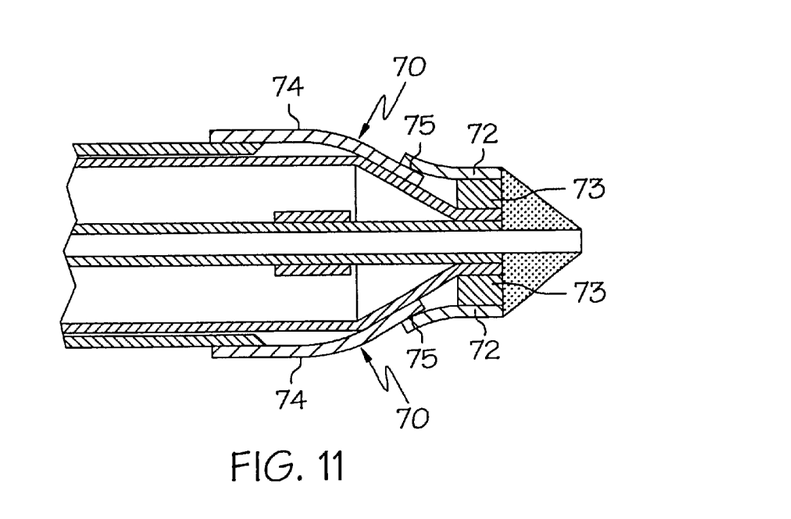
FIG. 11 is a view of a modification of the embodiment shown in FIG. 7.

In FIG. 11, sleeve 70 also comprises two pieces. The HM band 72 extends from being attached via conventional means to balloon at point 73 to a point partially up the cone portion of the balloon 14. The HM band 72 is in overlapping connection with the LM band 74 at point 75. The LM band 74 extends from point 75 to over the margin of the stent 20. In this embodiment, the HM band 72 overlaps the LM band 74.

Figure 12:
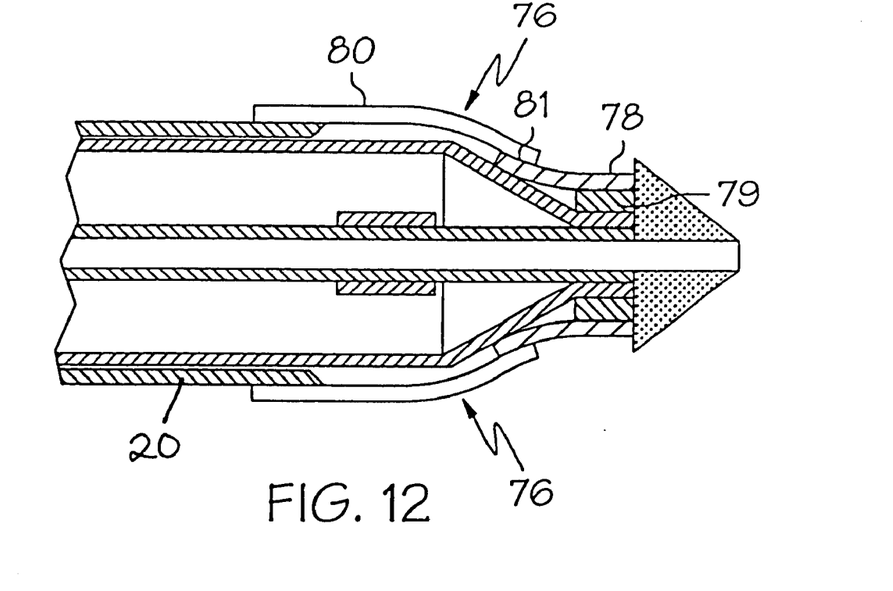
FIG. 12 is a view of a modification of the embodiment shown in FIG. 7.

In FIG. 12, sleeve 76 also comprises two pieces. The HM band 78 extends from being attached via conventional means to balloon at point 79 to a point partially up the cone portion of the balloon 14. The HM band 78 is in overlapping connection with the LM band 80 at point 81. The LM band 74 extends from point 81 to over the margin of the stent 20. In this embodiment, the LM band 80 overlaps the HM band 78.

It should be understood that the present application contemplates embodiments as described above where the LM bands and the HM bands are exchanged.

It should also be understood that the sleeves may be attached to the catheter or the waist portions of the balloon, for example at point 73, via adhesion or in direct contact via welding.

Figure 13:
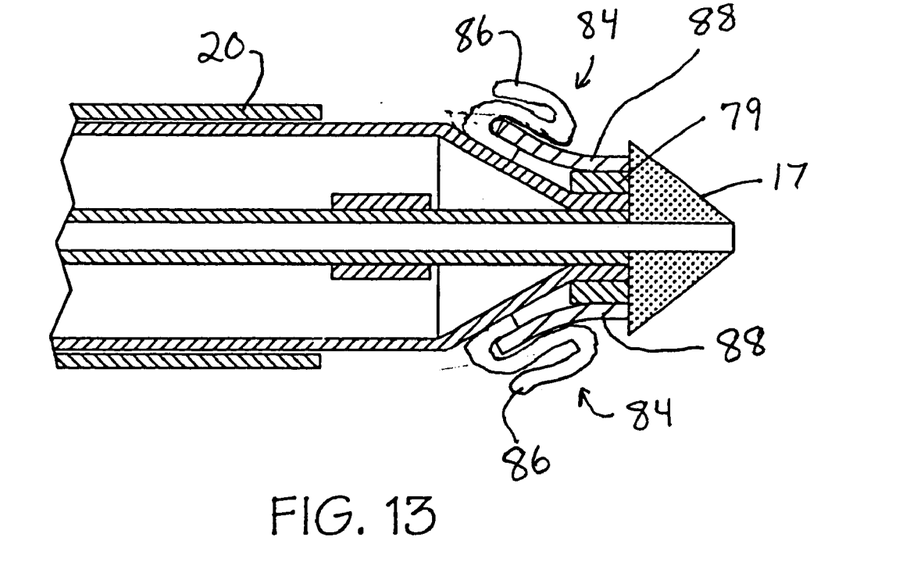
FIG. 13 is similar to FIG. 11 in which the balloon is expanded and the stent has been released.
Figure 14:
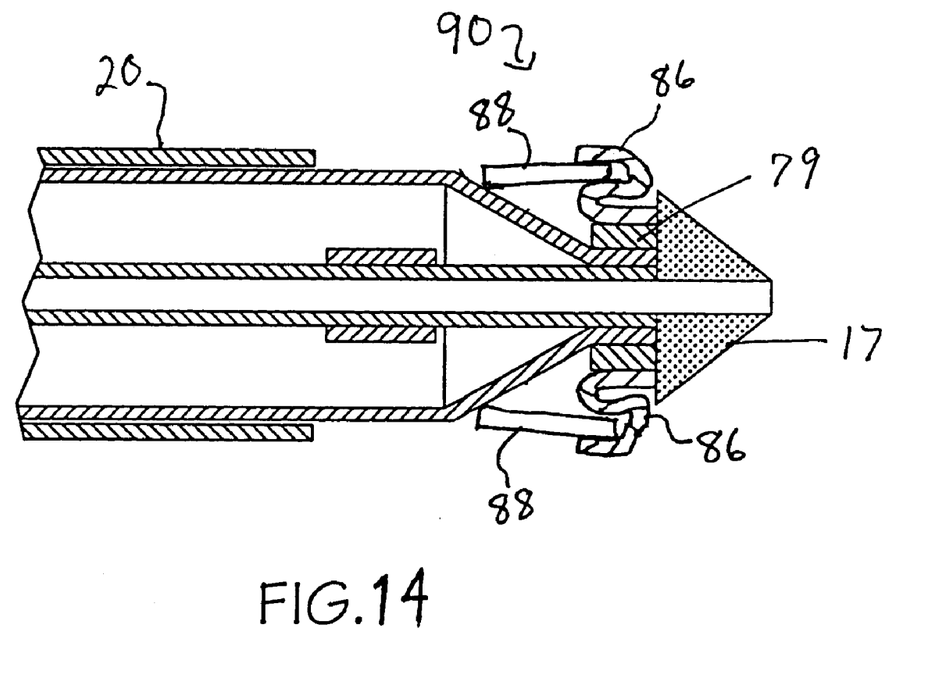
FIG. 14 is an alternative embodiment of the apparatus shown in FIG. 13.

FIGS. 13–14 show examples of the retraction of the sleeves when the balloon is expanded. The size of the balloons appear to be constant, however, it should be understood that the illustration is directed to the action of the sleeves during expansion and deployment of the stent.

In FIG. 13 the sleeve 84 comprises a LM band 86 and a HM band 88. During expansion of the balloon 14, the sleeve 84 recedes, or folds back onto itself. In this embodiment, the LM band 86 comprises a majority of the recession, while the HM band 88 retains more of its original shape. This is due in part to the relative stiffness of the HM band 88 as compared to the LM band 86. The exact manner in which the sleeves recede may vary. FIG. 14 illustrates a similar recession of an alternative sleeve wherein the LM bands 86 are attached to the catheter at point 79 and the HM bands 88 extend further onto the balloon. Similarly, the LM band 86 has a greater tendency to recede than does the HM band 88.

All of the patent, applications or publications referred to above are herein incorporated by reference in their entirety.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to". Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each single dependent claim format which creates a dependency from a prior antecedent-possessing claim other than the specific claim listed in such dependent claim below (e.g. claim 6 may be taken as alternatively dependent from any of claims 2–5, claim 4 may be taken as alternatively dependent from claim 3; etc.).

What is claimed is as follows:

1. A catheter system comprising:
   a catheter comprising an expandable distal portion constructed and arranged for expanding the outer diameter of said catheter from a contracted state to an expanded state, the expandable distal portion having a first end, a second end and a center portion between the first and second ends;
   a stent positioned around said distal portion of said catheter, said stent having a contracted condition and being expandable to an expanded condition, and being sized in said contracted condition to closely surround said catheter in the contracted state, said stent having at least an end portion lying over said expandable portion of said catheter; and
   a stent retaining sleeve in the region of the distal portion of the catheter and positioned around the catheter, having a first end connected to the catheter, and a second end, the first end of the stent retaining sleeve being axially fixed relative to the first end of the expandable distal portion and the second end of the stent retaining sleeve lying over said end portion of said stent, wherein the stent retaining sleeve comprises:
      a first sleeve in the region of said distal portion of said catheter and positioned around said catheter, having a first end connected to said catheter, and a second end; and
      a first band bonded to the first sleeve, wherein a portion of the first sleeve is positioned between the first band and the expandable distal portion of the catheter, the first band being positioned entirely between the first end and the second end of the first sleeve.

2. The catheter system of claim 1, the second end of the first sleeve lying over said end portion of said stent.

3. The catheter system of claim 2 wherein said expansible distal portion comprises a balloon having at least one cone portion mounted on a shaft of the catheter and wherein the first band is positioned over the cone portion when the balloon is in its contracted state.

4. The catheter system of claim 3 wherein said stent is expanded by expansion of said balloon.

5. The catheter system of claim 3, said first sleeve being formed from polyurethane.

6. The catheter system of claim 3, said first sleeve being formed from any elastomer able to be expanded with a balloon angioplasty catheter, and formable into a thin-walled tube.

7. The catheter system of claim 3, wherein the first band comprises a high modulus material relative to the first sleeve material.

8. The catheter system of claim 7, further comprising a second band bonded to the first sleeve over the cone portion of the balloon, positioned between the first sleeve and the balloon, wherein the second band comprises a high modulus material relative to the first sleeve material.

9. The catheter system of claim 8, said bands being formed in the shape of a coil.

10. The catheter system of claim 3, wherein the first band comprises a metal.

11. The catheter system of claim 3, wherein the first band is fully embedded with the first sleeve over the cone of the balloon.

12. The catheter system of claim 11 wherein the first band comprises a high modulus material having a Shore D scale hardness of equal to or greater than 55.

13. The catheter system of claim 3 wherein the first sleeve comprises a material selected from the group consisting of urethanes, styrenics, silicones, natural rubbers, nylons, latex, polyether amides and polyolefin copolymers, and wherein the first sleeve material has a Shore D scale hardness of 70A-55D.

14. The catheter system of claim 3 wherein the first band comprises a high modulus material having a Shore D scale hardness of equal to or greater than 55.

15. The catheter system of claim 3, wherein said first sleeve covering said end of said stent on said catheter when said catheter is in the contracted state, said catheter and stent cooperatively constructed and arranged for expansion of said catheter from said contracted state to said expanded state and to cause said first sleeve and first band to recede relatively axially, drawing said first sleeve from over said stent, thereby releasing said end of the stent from said catheter.

16. The catheter system of claim 3 further comprising:
   a second sleeve in the region of said distal portion of said catheter and positioned around said catheter, having a first end connected to said catheter, and a second end lying over an end portion of said stent, the second sleeve opposingly situated relative to the first sleeve; and
   a second band bonded to the sleeve, wherein a portion of the second sleeve is positioned between the second band and the expandable distal portion of the catheter, wherein the second band comprises a high modulus material relative to the second sleeve material and said second sleeve covering said end of said stent on said catheter when said catheter is in the contracted state, said catheter and stent cooperatively constructed and arranged for expansion of said catheter from said contracted state to said expanded state and to cause said second sleeve and second band to recede relatively axially, drawing said second sleeve from over said stent, thereby releasing said end of the stent from said catheter.

17. The catheter system of claim 1, wherein first end of the stent retaining sleeve is bonded to the first end of the expandable distal portion.

18. A catheter system comprising:
   a catheter comprising an expandable distal portion constructed and arranged for expanding the outer diameter of said catheter from a contracted state to an expanded state, said expandable distal portion being a balloon having at least one cone portion;
   a first sleeve in the region of said distal portion of said catheter and positioned around said catheter, having a first end gripped to said catheter, and a second end, said first sleeve comprising a first member and a second member, said members both having first and second ends, the first sleeve further comprising a first band of high modulus material relative to the members, wherein the first end of the first member is gripped to the catheter and the second end of the first member is connected to the first band and wherein the first end of the second member is connected to the first band, whereby the first band is between the first and second members.

19. The catheter system of claim 18, further comprising a stent positioned around said distal portion of said catheter, said stent having a contracted condition and being expandable to an expanded condition, and being sized in said contracted condition to closely surround said catheter in the contracted state, said stent having at least an end portion lying over said expandable portion of said catheter, wherein the second end of the second member extends over an end of the stent.

20. The catheter system of claim 19, further comprising a second sleeve in the region of said distal portion of said catheter and positioned around said catheter, the second sleeve being opposingly situated relative to the first sleeve and having a first end gripped to said catheter, and a second end lying over a second end portion of said stent, said second sleeve comprising a first member and a second member, said members both having first and second ends, the second sleeve further comprising a first band of high modulus material relative to the members, wherein the first end of the first member is gripped to the catheter and the second end of the first member connected to the first band and wherein the first end of the second member is connected to the first band and the second end of the second member extends over an end of the stent.

21. The catheter system of claim 20, wherein the first bands comprise a high modulus material having a Shore D scale hardness of equal to or greater than 55.

22. The catheter system of claim 18, the balloon having a first end, a second end and a center portion between the first and second ends, wherein at least one cone portion is positioned between the first end and the center portion of the balloon, the catheter system further comprising a stent positioned around the balloon, said stent having a first end portion, a second end portion and a contracted condition, the stent being expandable from the contracted condition to an expanded condition and being sized in said contracted condition to closely surround said balloon in the contracted state, the first end of the first sleeve being axially fixed relative to the first end of the balloon and the second end of the first sleeve lying over an end portion of said stent.

23. The catheter system of claim 18, wherein first end of the first sleeve is bonded to the first end of the balloon.

* * * * *